United States Patent
Le Van Mao

(10) Patent No.: US 11,780,797 B2
(45) Date of Patent: Oct. 10, 2023

(54) CATALYTIC CONVERSION OF LIGNOCELLULOSIC BIOMASS INTO INDUSTRIAL BIOCHEMICALS

(71) Applicant: Les Exploitations J.Y.B. Papineau Inc., Ferme-Neuve (CA)

(72) Inventor: Raymond Le Van Mao, Saint-Laurent (CA)

(73) Assignee: 11127012 CANADA INC., Quebec (CA)

( * ) Notice: Subject to any disclaimer, the term of this patent is extended or adjusted under 35 U.S.C. 154(b) by 0 days.

(21) Appl. No.: 17/590,108

(22) Filed: Feb. 1, 2022

(65) Prior Publication Data

US 2022/0153680 A1 May 19, 2022

Related U.S. Application Data

(62) Division of application No. 16/087,554, filed as application No. PCT/CA2017/050361 on Mar. 22, 2017, now Pat. No. 11,236,038.

(Continued)

(51) Int. Cl.
  *C07C 51/09* (2006.01)
  *C07C 67/39* (2006.01)
  (Continued)

(52) U.S. Cl.
  CPC ............. *C07C 51/09* (2013.01); *C07C 51/00* (2013.01); *C07C 51/285* (2013.01); *C07C 67/08* (2013.01); *C07C 67/39* (2013.01); *C07C 67/02* (2013.01)

(58) Field of Classification Search
  CPC ....... C07C 51/00; C07C 51/09; C07C 51/285; C07C 53/124
  See application file for complete search history.

(56) References Cited

U.S. PATENT DOCUMENTS 8,148,553 B2 * 4/2012 Dumesic .................. C10G 3/45
  585/324

FOREIGN PATENT DOCUMENTS

CA 2872510 11/2013
GB 2517338 A 2/2015
(Continued)

OTHER PUBLICATIONS

Hayes, D.J. et al., The Biofine Process—Production of levulinic acid, furfural, and formic acid from lignocellulosic feedstocks, Biorefineries—Industrial Processes and Products, Status Quo and Future Directions, vol. 1, Wiley-VCHk Verlag GmbH & Co, pp. 139-164 (Year: 2006).*

(Continued)

*Primary Examiner* — Yate' K Cutliff
(74) *Attorney, Agent, or Firm* — RYAN KROMHOLZ & MANION, S.C.

(57) ABSTRACT

This invention relates to a method for the conversion of lignocellulosic biomass into ethyl esters of carboxylic acids. Said method consists of treating the biomass material with an oxidizing agent that is incorporated in an solution comprising one or more acids, one or more alcohols and water, and subsequently performing a catalytic reaction at a higher temperature using the same acidic solution into which a larger volume of alcohol is added, in such a way that the catalytic conversion occurs in a medium with a much higher concentration of alcohol, i.e. with a much higher alcohol-to-water wt ratio. Such a method results in relatively high yields of ethyl esters, such as ethyl esters of formic, acetic, and levulinic acids, while producing a low yield of dialkyl ethers, which are unwanted by-products. The concentration of the oxidizing agent in the pre-treatment step is preferably higher than 6.0 wt %. The oxidizing agent is preferably a Fenton or Fenton-type reagent, and most preferably hydro- (Continued)

gen peroxide activated by Fe (II), and/or Ti (IV) ions. The alcohol is preferably ethanol, and when ethanol is used, diethyl ether is formed as the unwanted dialkyl ether by-product. Preferably, the biomass material is pelleted before treatment.

2 Claims, 2 Drawing Sheets

Related U.S. Application Data

(60) Provisional application No. 62/312,732, filed on Mar. 24, 2016.

(51) Int. Cl.
*C07C 67/08* (2006.01)
*C07C 51/00* (2006.01)
*C07C 51/285* (2006.01)
*C07C 67/02* (2006.01)

(56) References Cited

FOREIGN PATENT DOCUMENTS

| WO | WO2012/131665 A1 * | 10/2012 | ............... D21C 1/08 |
| WO | WO 2013/127006 A1 | 9/2013 | |
| WO | WO2014/144588 A1 * | 9/2014 | ............... C13K 1/02 |
| WO | WO 2014/144588 A1 | 9/2014 | |
| WO | WO 2015/017869 A1 | 2/2015 | |

OTHER PUBLICATIONS

Hayes, D.J.; Fitzpatrick, S ; Hayes, M.H.B.; Ross, J. R. H.; The Biofine Process—Production of Levulinic Acid, Furfural, and Formic Acid from Lignocellulosic Feedstocks, in Biorefineries-Industrial Processes and Products. Status Quo and Future Directions. vol. 1, Wiley-VCH (2006) p. 139-164.

Le Van Mao, R.; Zhao, Q.; Dima, G.; Petraccone, D.; New Process for the Acid-Catalyzed Conversion of Cellulosic Biomass (AC3B) into Alkyl Levulinates and Other Esters Using a Unique One-Pot System of Reaction and Product Extraction. Catal. Lett. (2011) 141, 271-276; and refs. therein.

Le Van Mao, R.; Muntasar, A.; Petraccone, D.; Yao, H.T.; AC3B Technology for Direct Liquefaction of Lignocellulosic Biomass: New Concepts of Coupling and Decoupling of Catalytic/Chemical Reactions for Obtaining a Very High Overall Performance. Catal. Lett. (2012) 142, 667-675.

Xiang et al, Oxidative Cracking of Precipitated Hardwood Lignin by Hydrogen Peroxide, Applied Biochemistry and Biotechnology (2000) vol. 84-86, 153-162.

International Search Report and Written Opinion pertaining to PCT/CA2017/050361, dated Jun. 27, 2017, 16 pgs.

* cited by examiner

CATALYTIC CONVERSION OF LIGNOCELLULOSIC BIOMASS INTO INDUSTRIAL BIOCHEMICALS

RELATED APPLICATIONS

This application is a divisional of application Ser. No. 16/087,554, filed 21 Sep. 2018 (now U.S. Pat. No. 11,236, 038), which is the US National Phase of PCT/CA2017/050361, which claims priority to provisional application Ser. No. 62/312,732 filed 24 Mar. 2016.

FIELD OF THE INVENTION

This invention relates to a method for the conversion of lignocellulosic biomass into valuable species such as ethyl esters of carboxylic acids.

BACKGROUND

Lignocellulosic materials include materials such as wood, wood wastes, forestry residues, paper-making or cardboard-making residues, agricultural residues, municipal waste, and perennial grasses. These materials mainly contain cellulose, hemicellulose, and lignin in various proportions.

There are known ways of converting lignocellulosic biomass materials into fuels and chemicals. In the case of wood and wood residues, it is known to convert such materials by first subjecting these to a chemical pre-treatment to disrupt the protective and chemically recalcitrant lignin layer. This allows access to cellulose and hemicellulose layers by chemical or enzymatic species being incorporated in a subsequent hydrolysis step. Thus, sugars (mainly glucose) can be extracted to produce, for example, bioethanol by enzymatic fermentation.

It is also known to use harsher conditions, such as stronger acids, for acid hydrolysis of cellulose and hemicellulose of lignocellulosic biomass. This results in the formation of carboxylic acids such as formic acid, levulinic acid, acetic acid, and furfural. Such chemical degradation is industrially exploited in the Biofine process [Reference 1].

Production of Alkyl Levulinates and Other Alkyl Esters:

Catalytic conversion of cellulose and hemicellulose into alkyl levulinates and light alkyl esters is currently known to be carried out in a) a single step process or b) a two-step process [Reference 2]).

In a typical single step process, alcohol is used as a reactant and solvent. At least one acidic catalyst is used, typically a mineral acid diluted in alcohol. The liquid products of the reaction consist of alkyl levulinate, alkyl formate, alkyl acetate, and 2-furfural (2-furfuraldehyde). The use of alcohol allows the occurrence of two chemical reactions: alcoholysis and esterification. However, the by-product dialkyl ether is also produced directly from the alcohol in significant amounts, said amounts varying with the process conditions such as temperature and exposure time. If the alcohol is ethanol, this ether is diethyl ether (ethyl ether). Diethyl ether, because of its high volatility at room temperature, is generally considered as an inconvenience in various process operations (such as handling and storage), and because of its low commercial value and limited market demand. Solid residues (commonly called lignin char) are also produced in significant quantities.

In a typical two-step process, both catalytic steps involve acid catalysts. The first step is the hydrolysis of cellulose and hemicellulose: this catalytic reaction uses water as a solvent, and produces levulinic acid as well as by-products such as formic acid, acetic acid, and 2-furfural. Most of the water is subsequently withdrawn from the reaction medium and replaced with ethanol [Reference 2]. Thus, esterification (of the resulting carboxylic acids) occurs in the second step, producing alkyl esters. Under some harsh conditions, 2-furfural resulting from the acid catalyzed degradation of the reaction intermediates of hemicellulose is partially converted into formic acid.

In a previous patent application entitled "Catalytic conversion of lignocellulosic biomass into fuels and chemicals" [Reference 3] and a 2012 publication in Catalysis Letters [Reference 4], preference was given to a single step process. In that invention, two novelties were introduced to the conventional approach:

a) The liquid product (esters) yields were significantly increased by having a Fenton reagent directly incorporated into the acidic ethanol solution. It is to note that the Fenton reagent comprised an oxidant (hydrogen peroxide, $H_2O_2$), coupled with Fe (II) and/or Ti (IV) ions [References 2, 3]. The incorporation of a Fenton reagent in the conventional acid catalyzed hydrolysis/ethanolysis of cellulose and hemicellulose did not significantly change the products spectrum, i.e. the same esters and oxygenates were produced, although in higher yields. In addition, some methanol was produced when Fenton reagents were used.

b) The unwanted diethyl ether was removed from the product liquids and then sent over a ZSM-5 based catalyst for its conversion into hydrocarbons [References 3, 4].

In that invention, the incorporation, of the Fenton reagent in the conversion medium resulted in a rapid and important size reduction of the biomass materials, such a phenomenon being accompanied by a sudden, albeit limited, rise in temperature and pressure. This was indicative of some destructive action due to the free radicals generated by the Fenton reagent.

The total product yield of the process increased with increasing amount of Fenton reagent, particularly with increasing the proportion of hydrogen peroxide. However, due to its relatively high cost, the increase in hydrogen peroxide consumption results in higher production costs.

It is also known from WO 2014/144588 to treat biomass in other to increase the porosity of cellulosic material, remove lignin for treatment into sugars followed by optional acid hydrolysis. A pre-treatment using ionic liquids is used to swell the biomass prior to an second step alkaline treatment to release the lignin and a third step or acid or enzymatic hydrolysis. The ionic liquids are selected from cation structures that include imidazolium, pyrroldinium, pyridinium, phosphonium, ammonium, or functionalized analogs thereof [Reference 5].

Finally, it is also know from CA 2872510 to pre-treat biomass by mechanical breakdown which does not substantially affect the lignin, cellulose and hemicellulose compositions of the biomass. Acid extraction is used to generate a sugar stream which is then treated with an amine extractant to remove impurities. [Reference 6].

Therefore, there is a need for an improved method that allows for the conversion of lignocellulosic biomass into ethyl esters of carboxylic acids, wherein the production of the DEE by-product is minimized; and wherein there is a decrease in the consumption of oxidizing agent.

SUMMARY OF THE INVENTION

This invention relates to a method for the conversion of lignocellulosic biomass into ethyl esters of carboxylic acids.

Said method consists of first treating the biomass material with an oxidizing agent in an acidic solution of alcohol and water, and subsequently performing a catalytic reaction at a higher temperature using the same acidic solution into which a large volume of alcohol is added. Accordingly, the catalytic conversion occurs at a much higher concentration of alcohol, i.e. with a much higher alcohol-to-water wt ratio.

The invention thus provides the following according to aspects thereof:

A method for converting lignocellulosic biomass materials into ethyl esters, said method comprising the following steps:
  a) thermo-chemical pre-treatment of the biomass materials with an oxidizing agent solubilized in an acidic solution comprising an acid, an alcohol, and water, thereby forming a pre-treatment slurry;
  b) diluting the slurry with additional alcohol and optionally additional acid species, such as sulfuric acid, obtaining catalytic conversion of the biomass materials in the slurry into ethyl esters; and
  c) recovery of the resulting products, wherein the resulting products include the ethyl esters.

Other objects, advantages and features of the present invention will become more apparent upon reading of the following non-restrictive description of specific embodiments thereof, given by way of example with reference to the accompanying drawings.

DETAILED DESCRIPTION OF THE INVENTION

To provide a clear and consistent understanding of the terms used in the present specification, a number of definitions are provided below. Moreover, unless defined otherwise, all technical and scientific terms as used herein have the same meaning as commonly understood to one of ordinary skill in the art to which this disclosure pertains.

The use of the word "a", "an" or "the" when used in conjunction with the term "comprising" in the claims and/or the specification may mean "one", but it is also consistent with the meaning of "one or more", "at least one", and "one or more than one".

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, un-recited elements or process steps.

As used herein the term "about" is used to indicate that a value includes an inherent variation of error for the device or the method being employed to determine the value. In the present application, reference to numerical values are understood to be approximate or about that value owing to normal variations in methodology or measurements. Unless otherwise indicated, the term "about" will allow plus or minus variations of 10%. Unless otherwise indicated the reporting of numerical value are understood to be approximate regardless of the use of the word "about" in relation to the numerical value.

Figure 2:
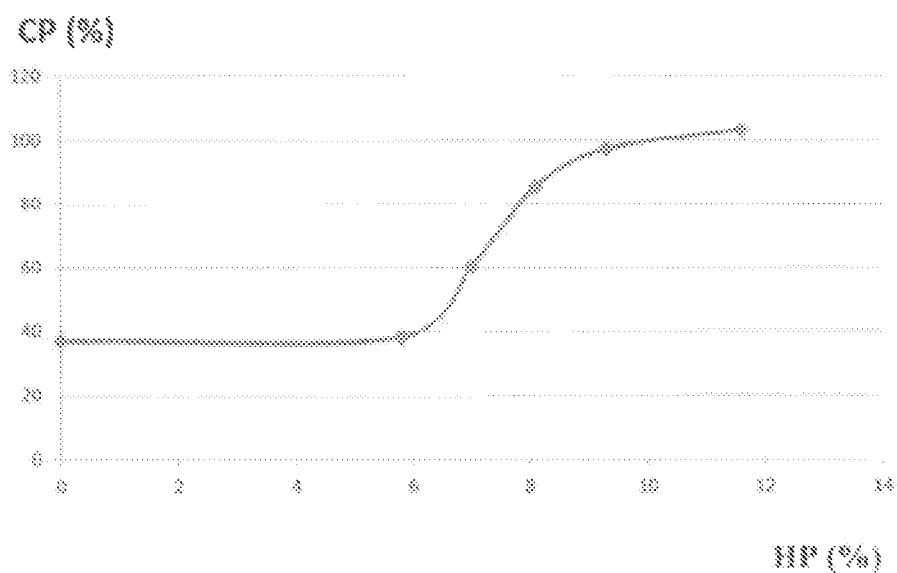
FIG. 2 shows the variation of the total product yield CP (in wt %, with the exclusion of the diethyl ether, DEE, yield) as a function of the concentration of oxidant ($H_2O_2$) in a Fenton reagent (HP, expressed in wt of the catalytic conversion solution), in accordance with an example of a method known in the prior art.

The data of FIG. 2 and the observed phenomena as reported in paragraph (9) suggests that the disruptive action of the free radicals (being generated by an oxidizing agent, preferably a Fenton or a Fenton type reagent) on the lignin layer of the biomass material, occurs in the liquid phase. Moreover, for such solution to be efficient, its oxidizing agent concentration, preferably $H_2O_2$ concentration, is preferably higher than 6 wt %.

The present invention incorporates into the process a pre-treatment step aimed at degrading the biomass structure. Essentially, this step is carried out with a liquid solution having a much smaller volume than that used in the prior art. However, the related volume is preferably sufficient to keep the biomass material totally immersed into that liquid. As a result, it is possible to maintain an oxidizing agent concentration, preferably a $H_2O_2$ concentration, higher than about 6 wt while considerably reducing the amount of the oxidizer used. The present invention also supposes that the oxidizing agent, preferably $H_2O_2$, does not need to intervene in the subsequent step of "hydrolysis-esterification" (catalytic conversion), which requires a larger liquid volume and a higher reaction temperature.

In one embodiment of the present invention, the method comprises the following steps:
  a) Biomass pre-treatment: is carried out by submitting the biomass material to a combined effect consisting of the degradation of the biomass structure by an oxidizing agent, preferably a Fenton reagent, and by an acidic species. A minimal amount of liquid should be used in order to have a concentration of oxidizing agent higher than about 6 wt % while having the biomass material essentially all immersed in the liquid. However, in this phase, neither water nor alcohol can be used alone because the next step of the method includes several catalytic reactions (biomass hydrolysis/esterification), thereby requiring water and alcohol, preferably ethanol, in well defined proportions. Thus, the pre treatment phase is done in an acidic solution of alcohol, preferably ethanol, and water, and in the presence of an oxidizing agent, preferably a Fenton reagent: all these components are preferably incorporated into the reaction medium with precise timing. The maximum temperature used is preferably about 150° C., which is also the boiling point of hydrogen peroxide.
  b) Final biomass conversion: this step is performed over the resulting degraded biomass at a higher temperature, preferably at around 180° C., upon addition of alcohol, preferably ethanol, and adjustment of the acidity. In such a context, water is used as a dialkyl ether inhibitor, preferably a DEE inhibitor if ethanol was used. However, the amount of water is preferably regulated because if there is too much water in the reaction medium, it may negatively affect the total product yield. Finally, some polymerization inhibitor can be added in order to prevent an excessive formation of polymeric species that may contribute to some decrease in the final product yields.

Figure 1:
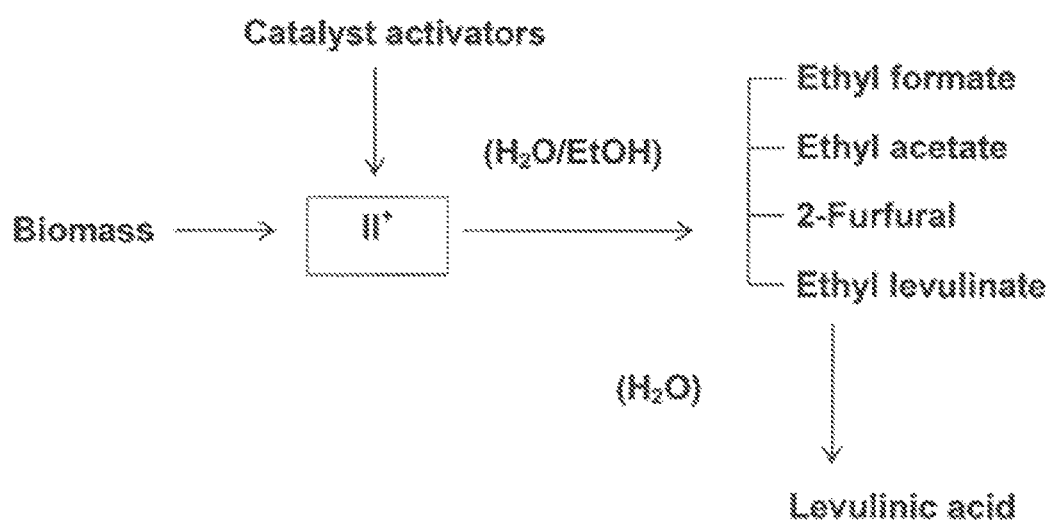
FIG. 1 shows the general conversion method of an embodiment of the present invention.

FIG. 1 shows the general conversion scheme of a specific embodiment of the present invention, illustrating controlled use of Fenton or Fenton-type reagents during a biomass pre-treatment phase, thus allowing a subsequent catalytic reaction to produce ethyl esters in relatively high yields. It also illustrates the use of acidic solutions of alcohol and water in both pre-treatment and conversion phases, which can drastically reduce the formation of dialkyl ethers, an unwanted by-product.

The method of the present invention results in relatively high yields of ethyl esters, preferably ethyl esters of formic, acetic, and levulinic acids, while producing a low yield of dialkyl ethers, unwanted by-products. Thus, the method of the present invention shows two important practical advantages when compared to that of the prior art that also made use of oxidizing agents: a) there is a reduction in unwanted by-products with basically no or little need of up-grading the unwanted dialkyl ethers; and b) the process consumption of oxidizing agent is greatly reduced.

According to one embodiment of the present invention, the concentration of the oxidizing agent used in the biomass pre-treatment phase is preferably above about 6.0 wt %.

In a further embodiment of the present invention, the use of a polymerization inhibitor in step b) is preferred.

In yet another embodiment of the present invention, the method results in relatively high yields of ethyl esters of formic, acetic, and levulinic acids, and a significant production of levulinic acid, furfural, methanol, α-angelica-lactone, methyl levulinate and dialkyl succinate.

In an additional embodiment of the present invention, the "water-to-alcohol" weight ratio in the reaction medium has some influence on the products' "levulinic acid-to-ethyl levulinate" weight ratio. Interestingly, it is possible to limit the production of dialkyl ethers to an acceptable level by adjusting the reaction parameters, particularly by adjusting the "water-to-alcohol" weight ratio in the main conversion step.

In another embodiment of the present invention, it is possible to further reduce the volume of the liquid phase used in the pre-treatment step, while maintaining a sufficiently high oxidizing agent concentration, preferably $H_2O_2$ concentration, by increasing the bulk density of the biomass material prior to submitting it to the pre-treatment operation. In fact, "pelleting" or "pelletizing" these materials can significantly increase their specific density. This in turn allows to use less liquid to achieve immersion of a given volume of biomass material. Such a densification of biomass materials can be carried out with a binder (rice-husk pellets) or without a binder (wood pellets). In addition to an advantageous reduction of the consumption of the oxidizing agent, this pelleting can reduce the overall volume of other reagents (including acid species) and solvents used in the process.

The invention is illustrated in further detail by the following non-limiting examples.

Examples 0-5 (Comparative)

In prior art methods using a Fenton reagent, wherein said Fenton reagent is directly added to the reaction medium to enhance the production of alkyl esters [References 3, 4], high concentrations of the oxidant (hydrogen peroxide) in the conversion solution were needed to achieve high yields of alkyl esters. Otherwise, in the absence of the Fenton reagent, such yields were quite low. FIG. 2 and Table 1 report the results obtained with these known methods.

FIG. 2 shows the variation of the total product yield CP (in wt %, with the exclusion of the diethyl ether, DEE, yield) as a function of the concentration of the oxidant ($H_2O_2$) in the Fenton reagent (HP, expressed in wt % of the conversion solution), in accordance with an example of a prior art method.

The corresponding values of HP and CP, as well as B/HP (biomass-to-hydrogen peroxide wt ratio) are reported in Table 1:

TABLE 1

Total product yield versus $H_2O_2$ concentration HP

| | Example number | | | | | |
|---|---|---|---|---|---|---|
| | 0 | 1 | 2 | 3 | 4 | 5 |
| HP ($H_2O_2$) | 0 | 5.7 | 7.3 | 8.1 | 9.3 | 11.6 |
| B/HP | — | 3.6 | 2.8 | 2.6 | 2.2 | 1.8 |
| CP | 37 | 38 | 60 | 85 | 97 | 103 |

Note:
(there is no pre-treatment step in the prior art method)

Thus, HP has an important influence on the total product yield (CP).

FIG. 2 shows that the total product yield starts steadily increasing when the value of HP is higher than about 6.0, corresponding to a value of B/HP lower than about 3.3 (Table 2). The latter parameter indicates that at least 30 g of hydrogen peroxide are needed for obtaining a total product yield CP higher than 38 wt (conventional value reported when Fenton reagents are not in use).

Table 2 shows some typical results obtained with the prior art method:

TABLE 2

Typical performances of the catalytic conversion of spruce chips, in accordance with the method of the previous invention

| | Example number | | |
|---|---|---|---|
| | 0 | 2 | 4 |
| HP | 0 | 7.3 | 9.3 |
| B/HP | — | 2.8 | 2.2 |
| $H_2O_2$ consumed in g per 100 g of dried biomass | 0 | 36 | 45.5 |
| Product yield (wt %) | | | |
| Ethyl formate | 5 | 17 | 37 |
| Ethyl acetate | 4 | 14 | 24 |
| Ethyl levulinate | 18 | 20 | 22 |
| Methanol | 0 | 3 | 5 |
| 2-furfural (and other oxygenates) | 1 | 5 | 9 |
| CP | 28 | 59 | 97 |
| Diethyl ether (DEE) | 64 | 52 | 60 |

Thus, in accordance with the prior art, higher product yields (particularly for short esters, i.e. ethyl formate and ethyl acetate) are obtained with higher concentrations of hydrogen peroxide HP, leading to higher total product yield CP (excluding DEE). Unfortunately, the yield of DEE is also very high.

Typical Procedure used for the Biomass Catalytic Conversion of the Previous Invention (Example 4 of Table 1 and Table 2)

45.0 g of spruce wood chips (dried in an oven at 80° C. for 48 hours), were added to solution A, being contained in a Parr reactor (capacity=1 liter) and made from 132 g of absolute ethanol and 41 g of aqueous hydrogen peroxide (50% $H_2O_2$), equivalent to 45.5 g of $H_2O_2$ per 100 g of dried biomass. Then, solution B, 2.0 g of ferrous sulphate heptahydrate dissolved in 24 g $H_2SO_4$ (17 wt and 17 q water, was slowly added under cooling and mild stirring.

Composition: liquid=215 g; liquid/biomass=4.8; $H_2O_2$ (HP)=9.3 wt %; acidity=1.9 wt ethanol/water=4.1; biomass/$H_2O_2$ (B/HP)=2.25 (meaning that for treating 100 g of biomass, 44 g of $H_2O_2$ were necessary).

Then, the autoclave was heated to the reaction temperature of 181° C. and maintained at said temperature for 60 min.

In the prior art method, due to high yields of the by-product diethyl ether (DEE), as reported in Table 2, the method needed a second catalytic step (conversion over a zeolite based catalyst) to convert the important amounts of DEE (DEE up-grading). In addition, the large consumption of hydrogen peroxide, which is quite expensive and not readily available, may significantly affect the production costs of valuable biochemicals, particularly that of ethyl levulinate.

Examples 6 (Comparative) and Examples 7-10

Data obtained using an embodiment of the method of the present invention are reported in Table 3 as Examples 7-8.

TABLE 3

Conversion of spruce chips using an embodiment of the present invention.

| | Example number | | |
|---|---|---|---|
| | 6 | 7 | 8 |
| HP (*) | NO | 6.6 | 6.6 |
| B/HP | — | 5.6 | 5.6 |
| Polymerization inhibitor | NO | NO | YES |
| Product yield (wt %) | | | |
| Ethyl formate | 7 | 13 | 14 |
| Ethyl acetate | 5 | 9 | 10 |
| Ethyl levulinate | 14 | 21 | 22 |
| Levulinic acid | 1 | 3 | 2 |
| Furfural | 3 | 1 | 1 |
| Methanol | 0 | 3 | 4 |
| Diethyl succinate & other oxygenates | 2 | 3 | 3 |
| DEE | 6 | 7 | 7 |
| CP (excluding DEE) | 32 | 54 | 56 |

Note:
HP (*) = concentration of $H_2O_2$ in the pre-treatment liquid phase, expressed as % wt.

In preferred embodiments of the present invention as illustrated by examples 7 to 10, the following procedure is provided for:

I) Pre-Treatment Step:

A given mass of biomass material is soaked with Solution A, wherein Solution A contains ethanol, sulfuric acid diluted in ethanol, and hydrogen peroxide. Afterwards, Solution B, containing ferrous sulfate dissolved in water, is rapidly added under cooling to form a slurry, so that the following conditions are satisfied:
  a) Liquid/biomass wt ratio=1.5-3.
  b) Hydrogen peroxide concentration=above 6.0 wt %.
  c) Acidity=2.0-4.0 wt %.
  d) The slurry is heated in an autoclave at a temperature between 85° C. to 145° C. for 1 to 5 hours.

II) Catalytic Conversion Step:

Solution C, containing sodium sulfite dissolved in water, and solution D, containing ethanol and eventually some sulfuric acid diluted in ethanol, are successively added.
In step II), the reaction conditions are as follows:
  a) Liquid/biomass wt ratio=3.5 7.0
  b) Acidity=1.2-2.3 wt %.
  c) Ethanol/water wt ratio=3.5-5.5
  d) Reaction temperature=170° C.-190° C.
  e) Reaction time=25 min-120 min.

Table 3 shows that:
  a) The use of an oxidizing agent, preferably a Fenton or Fenton-type reagent, in the pre-treatment step, leads to higher yields of all ester products (Examples 7 and 8, versus Example 6), and to an increased production of methanol.
  b) Water in significant concentration in the conversion medium results in the production of valuable levulinic acid (for comparison, in all examples of Table 2, there is almost no levulinic acid produced), and is the most likely cause of the strong decrease in dialkyl ether production, which was DEE in this embodiment of the present invention (Examples 7 and 8 of Table 3 versus Examples 2 and 4 of Table 2).
  c) In Examples 7 and 8 of Table 3, the B/HP (biomass-to-hydrogen peroxide used) ratio has a value of 5.6, which is much higher than those reported in Examples 2 and 4 of Table 2 (prior art). This is because the amount of $H_2O_2$ added into the pre-treatment step is much smaller than the amount added to the conversion medium of the prior art (a process having no pre-treatment step). Here, a B/HP of 5.6 means that for treating 100 g of dried spruce chips, only 18 g of hydrogen peroxide are needed, as opposed to the 36 g of oxidizer (B/HP=2.6) used in Example 2 of Table 2, despite both examples having almost the same total product yield CP.
  d) The use of a polymerization inhibitor (sodium sulfite in Example 8 of Table 3) significantly increases the total product yield (Example 7 of Table 3). Another inhibitor that can be used is magnesium sulfite trihydrate.

Preferred Embodiment of Example 8 (Table 3)

a) Pre-treatment Step:

50.0 g of spruce wood chips, dried in an oven at 80° C. for 48 hours, were added to solution A, being contained in a Parr reactor (capacity=1 liter) and made from 40 g of $H_2SO_4$ dissolved in absolute ethanol (10 wt %), 56 g of absolute ethanol, and 18 g of aqueous hydrogen peroxide (50% $H_2O_2$). Then, solution B (1.1 g of ferrous sulphate heptahydrate dissolved in 22 g water) was slowly added under cooling and mild stirring to form a slurry.

Composition: total liquid=137.1 g; liquid/biomass=2.7; acidity=2.9 wt %, hydrogen peroxide=6.6 wt %; ethanol/water=2.3.

The slurry is then heated very slowly to 140° C. The temperature is held at that value for 2 hours.

b) Catalytic Conversion Step:

Solution C (1.4 g of sodium sulfite dissolved in 6 g of water) and solution D (12 g of $H_2SO_4$ dissolved in absolute ethanol (10 wt %)+97 g of absolute ethanol) were successively added.

Composition: liquid=254 g; liquid/biomass=5.1; acidity=2.0 wt %; ethanol/water=4.3.

The resulting solution is heated to 179° C. and that temperature is kept constant for 60 minutes.

The amount of oxidizing agent, advantageously hydrogen peroxide, used in the pre-treatment phase plays a role in the method of the invention. Table 4 shows the effect of the biomass-to-hydrogen peroxide wt ratio (B/HP) on the product yields. It is important to note that in all examples of Table 4, all reaction parameters are the same (see preferred embodiment of Example 8 of Table 3), except for the amount of hydrogen peroxide used in the pre-treatment phase, in that there is variation in the amount of hydrogen peroxide adjusted with water used in examples 9 and 10.

TABLE 4

Influence of the HP (*) and B/HP ratio on the product yields.

|  | Example number | | |
| --- | --- | --- | --- |
|  | 9 | 8 (**) | 10 |
| HP (*) | 7.3 | 6.6 | 5.8 |
| (B/HP) | 5.0 | 5.6 | 6.3 |
| $H_2O_2$ consumed/100 g dried Biomass | 20 | 18 | 16 |
| Product yield (wt %) | | | |
| Ethyl formate | 15 | 14 | 13 |
| Ethyl acetate | 12 | 10 | 9 |
| Ethyl levulinate | 23 | 22 | 21 |
| Levulinic acid | 3 | 2 | 2 |
| Furfural | 1 | 1 | 1 |
| Methanol | 4 | 4 | 3 |
| Diethyl succinate & others | 2 | 3 | 2 |
| DEE | 13 | 7 | 8 |
| CP (excluding DEE) | 60 | 56 | 51 |

HP (*) = concentration of $H_2O_2$ in the pre-treatment liquid phase expressed as % wt;
(**) same as Example 8 of Table 3;

When directly comparing Example 2 of Tables 1 and 2 (using the method of the prior art, References 3 and 4), and Example 8 of Tables 3 and 4 (using an embodiment of the method of the present invention), the following conclusions can be reached:
a) Both runs provide similar total product yields CP (excluding DEE).
b) The production of DEE with this embodiment of the method of the present invention is minimal in comparison to the prior art.
c) The consumption of hydrogen peroxide per 100 g of dried biomass with the method of the present invention is only about half of that of the prior art (18 g versus 36 g).

Thus, by using the method of the invention instead of that of the prior art, it is possible to very significantly decrease the amount of hydrogen peroxide used while obtaining almost the same yield of commercially valuable products, in particular ethyl levulinate.

In addition, the method of the invention when compared to that of the prior art, significantly decreases the amount of the "unwanted" DEE. It is to note that DEE is produced directly from ethanol by dehydration. Thus, "less DEE produced" means "lower ethanol consumption".

Significantly lower consumption of fed hydrogen peroxide and significantly lower consumption of fed ethanol mean lower production cost for the product esters.

The invention of a specific pre-treatment phase that uses a reduced liquid volume (with respect of the total volume of the main catalytic conversion phase) in conjunction with a sufficient concentration of hydrogen peroxide, allows further improvement of the process (by "densification" of the biomass feed). In fact, by reducing the size of the biomass chips, it is possible to increase the B/HP ratio (more biomass material converted for the same mass of hydrogen peroxide used).

An advantageous finding according to embodiments of the present invention was also noted: the final products obtained from the catalytic conversion step do no vary as a function of the impurities present in the initial biomass charge.

It is to note that there is no reaction with the Fenton Reagent when the temperature is equal or lower than 40° C. However, when the reaction vessel is heated at a temperature higher than 45° C., there is a spontaneous and quite rapid increase of temperature (to 105-110° C., generally at a rate of 20° C./min) and pressure (40-45 psi) that may help disrupting the ligno cellulosic structure of the biomass.

The method of the invention, when used with a biomass conversion medium containing only water (used as a solvent as in a conventional acid hydrolysis) leads to the same level of yield increase (mostly for levulinic acid). Therefore, this beneficial effect can be attributed to the action of the oxidizing agent, which in this embodiment of the present invention was a Fenton reagent.

Ethyl levulinate and its carboxylic acid, levulinic acid, have numerous commercial applications [2]. These compounds are considered as platform chemicals, meaning that they can lead to the production of numerous other industrial chemicals [2].

It is important to note that all ethyl esters obtained by the method of this invention (particularly ethyl formate and ethyl levulinate) can be converted into their corresponding carboxylic acids via known acid-catalysed hydrolysis. To do so, solid acidic catalysts such as zeolites and special acidic ion-exchange resins are preferred owing to some advantages associated with their use.

It is also important to note that diethyl ether DEE can be converted, if necessary, to other chemicals such as light olefins or ethyl acetate, or converted back to ethanol.

DEE can be converted to light olefins and heavier hydrocarbons (particularly, aromatics), over zeolite catalysts, particularly ZSM-5 zeolite (Si/Al ratio=from 40 to 60), at a temperature ranging from 280° C. to 320° C., and a W.H.S.V. (weight hourly space velocity), ranging from 1.0 $h^{-1}$ to 4.0 $h^{-1}$. It is advantageous to dilute DEE with water in the proportion (water/DEE) of 1/2 to 2/1 in order to reduce the rate of carbonaceous deposition onto the zeolite acid sites, minimizing thus the catalyst fouling. The latter phenomenon, if being important, needs a too frequent catalyst regeneration by combustion in air at elevated temperatures (450-550° C.). Total hydrocarbon yield can exceed 90 wt % is in most preferred operating conditions.

DEE can also be converted into ethyl acetate with acetic acid over an acidic catalyst. Solid acidic catalysts are preferred for easy products/catalyst separation reason. The most preferred solid acidic catalyst is the H-USY (acid form-ultra stabilized Y zeolite) for its structural robustness and its relatively high yield of ethyl acetate (more than 60 wt % at 300° C.).

DEE can also be converted back to ethanol with water over an acidic catalyst at high temperature and high pressure.

The method of this invention has characteristics for successful commercial development, i.e. simple, green, and sustainable technology, with low cost production of valuable chemicals used in various fields of chemical industry.

The scope of the claims should not be limited by the preferred embodiments set forth in the examples, but should be given the broadest interpretation consistent with the description as a whole.

The present description refers to a number of documents, the content of which is herein incorporated by reference in their entirety which is herein incorporated by reference in their entirety.

REFERENCES

[1] D J. Hayes, S. Fitzpatrick, M. H. B. Hayes, J. R, H. Ross, in Biorefineries-Industrial Processes and Products, Wiley-VCH (2006) p. 139-164.
[2] R. Le Van Mao, Q. Zhao, G. Dima, D. Petraccone, Catal. Lett, (2011) 141, 271-276; and refs. therein.
[3] R. Le Van Mao, WO 2013/127006 A1.
[4] R. Le Van Mao, A. Muntasar, D. Petraccone, H. T. Yao, Catal. Lett. (2012) 142, 667-675; and refs. therein.
[5] WO 2014/144588, Suganit Systems Inc.
[6] CA 2872510, Virdia Inc.

I claim:

1. A method for converting lignocellulosic biomass materials into carboxylic acids, the method comprising the follow steps:
    (a) thermo-chemical pre-treatment of the biomass materials with hydrogen peroxide solubilized in an acidic/aqueous medium, wherein a total liquid to biomass ration is 3 or less;
    (b) catalytic conversion with acidic species while in the aqueous medium in the presence of an alcohol; and
    (c) recovery of the resulting products.

2. The method of claim 1, wherein the carboxylic acids are one or more of levulinic acid, formic acid, and acetic acid.

* * * * *